(12) United States Patent
White et al.

(10) Patent No.: US 8,252,032 B2
(45) Date of Patent: Aug. 28, 2012

(54) BONE PLATE WITH COMPLEX, ADJACENT HOLES JOINED BY A RELIEF-SPACE

(75) Inventors: Patrick White, West Chester, PA (US); Steve Forbes, Exton, PA (US); Gary Thau, Morgantown, PA (US)

(73) Assignee: Swiss Pro Orthopedic SA, Bienne (CH)

( * ) Notice: Subject to any disclaimer, the term of this patent is extended or adjusted under 35 U.S.C. 154(b) by 803 days.

(21) Appl. No.: 12/307,451

(22) PCT Filed: Jul. 6, 2007

(86) PCT No.: PCT/IB2007/001895
§ 371 (c)(1),
(2), (4) Date: Mar. 6, 2009

(87) PCT Pub. No.: WO2008/007196
PCT Pub. Date: Jan. 17, 2008

(65) Prior Publication Data
US 2009/0292318 A1     Nov. 26, 2009

Related U.S. Application Data

(60) Provisional application No. 60/806,728, filed on Jul. 7, 2006, provisional application No. 60/806,730, filed on Jul. 7, 2006.

(51) Int. Cl.
*A61B 17/80* (2006.01)
(52) U.S. Cl. ............................ 606/280; 606/286
(58) Field of Classification Search .......... 606/70, 606/71, 280, 281, 286, 287, 288, 289, 291
See application file for complete search history.

(56) References Cited

U.S. PATENT DOCUMENTS

| | | | |
|---|---|---|---|
| 3,659,595 | A | 5/1972 | Haboush |
| 3,716,050 | A | 2/1973 | Johnston |
| 4,611,581 | A | 9/1986 | Steffee |
| 4,696,290 | A | 9/1987 | Steffee |
| 5,057,111 | A | 10/1991 | Park |
| 5,209,751 | A | 5/1993 | Farris et al. |
| 5,261,910 | A | 11/1993 | Warden et al. |
| 5,324,290 | A | 6/1994 | Zdeblick et al. |
| 5,364,399 | A | 11/1994 | Lowery et al. |

(Continued)

FOREIGN PATENT DOCUMENTS

EP       1468655 A2    10/2004

(Continued)

*Primary Examiner* — Cris L Rodriguez
*Assistant Examiner* — Eric Rosen
(74) *Attorney, Agent, or Firm* — Michael F. Scalise

(57) ABSTRACT

A bone plate is described which is adapted for use in situ to fix a spatial relationship of at least two bone parts. The bone plate has at least one pair of the bone screw apertures that are adjoined by a relief-space contiguous with the open space of the screw apertures themselves. An adjoined aperture pair forms a complex aperture and has a center-to-center distance of the apertures along an axis running through the centers of the apertures. The center-to-center distance is equal to or greater than the sum of the radii of the heads of the individual bone screw used with the aperture pair. At least one of the screw apertures has a screw head seat having at least one relief notch set into a surface of the screw head seat. The relief notch provides desirable advantages that are not similarly accomplished in their absence.

24 Claims, 7 Drawing Sheets

U.S. PATENT DOCUMENTS

| | | | |
|---|---|---|---|
| 5,681,311 A | 10/1997 | Foley et al. | |
| 5,709,686 A | 1/1998 | Talos et al. | |
| 6,406,478 B1 | 6/2002 | Kuo | |
| 6,669,701 B2 | 12/2003 | Steiner et al. | |
| 6,719,759 B2 | 4/2004 | Wagner et al. | |
| 7,220,263 B2 * | 5/2007 | Cordaro | 606/70 |
| 7,354,441 B2 | 4/2008 | Frigg | |
| 2002/0183752 A1 * | 12/2002 | Steiner et al. | 606/69 |
| 2004/0181228 A1 | 9/2004 | Wagner et al. | |
| 2005/0096657 A1 | 5/2005 | Autericque et al. | |
| 2005/0216027 A1 | 9/2005 | Suh et al. | |

FOREIGN PATENT DOCUMENTS

| | | |
|---|---|---|
| EP | 1468655 | 5/2006 |
| WO | 01/54601 A1 | 8/2001 |
| WO | 2006/014391 A1 | 2/2006 |

* cited by examiner

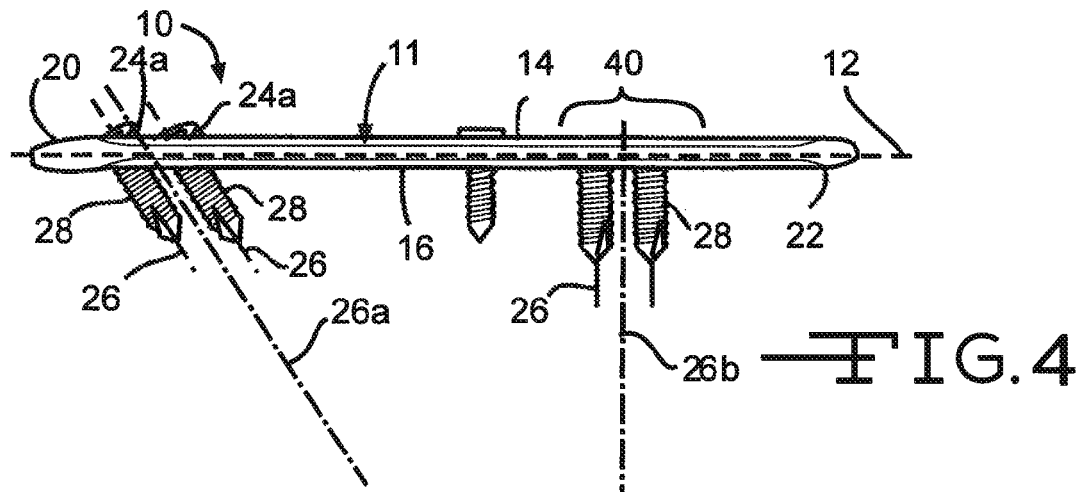
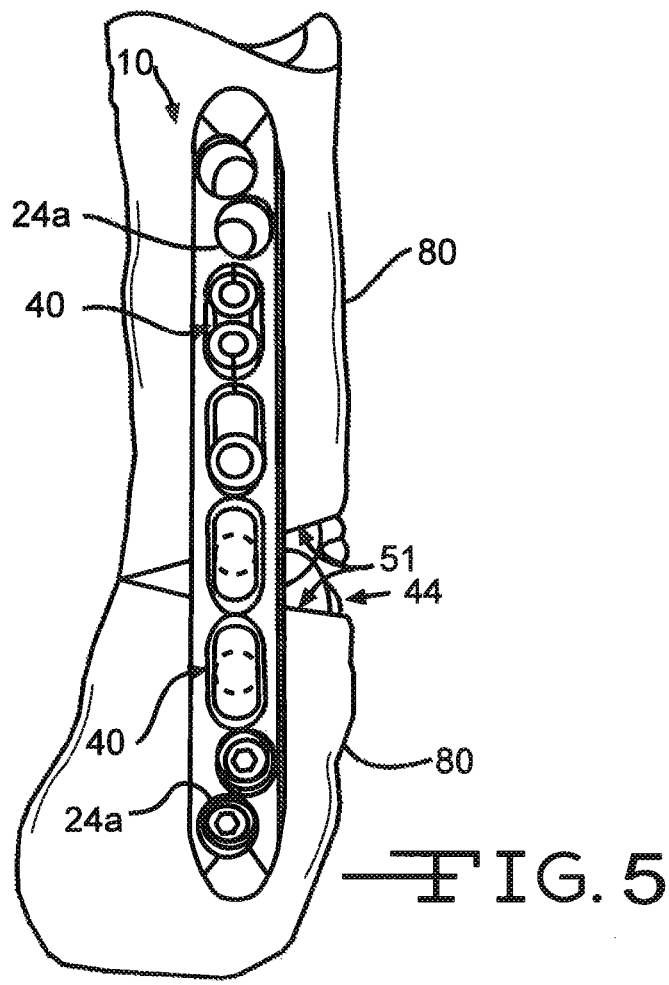

BONE PLATE WITH COMPLEX, ADJACENT HOLES JOINED BY A RELIEF-SPACE

CROSS-REFERENCE TO RELATED APPLICATIONS

The present application claims priority as a 371 of international application PCT/IB2007/001895, tiled on 6 Jul. 2007; which claims the benefit of prior filed U.S. Provisional Patent Application, serial numbers 60/806,728 filed 7 Jul. 2006, and 60/806,730 also filed 7 Jul. 2006.

FIELD OF THE INVENTION

The present invention is in the field of surgically implanted orthopedic devices, implants and prostheses used in orthopedic surgery. More specifically, the present invention relates to bone plates used to reinforce fractured bones and thus to promote healing.

BACKGROUND OF THE INVENTION

A compressive screw system, also known as the DCS system, is a bone plate system that has been used in trauma surgery for many years. The procedures for use of this system are well documented by the AO Institute (Davos, Switzerland), an institute having as one of its goals, the promotion of new orthopedic surgical procedures. This system included a bone plate having slots communicating therethrough. A land in which the slot is wider at one end defines a stepped surface adjacent the portion of the slot that extends through the bone plate. The stepped surface is generally cut with a spherical endmill, thus creating a spherical stepped surface.

In a still further development, there exists bone plates which have individual threaded and non-threaded apertures interspersed along the length of the plate. In this and other designs, the distance between holes has become a standard. Although an improvement over the inserts noted above, the locking positions are pre-defined and only available in limited locations, which also reduce surgical flexibility. In another product variation, expandable, lockable inserts enter into the slots of a standard bone plate. When the bone screw passes through one of these inserts and is torqued down, the insert expands and locks the screw in place. However, this insert is locked in a secondary operation. This is not desirable because this requires more operating room time and adds complexity to the procedure. Further, the inserts must be added in the specific location before the plate is fixed to the bone and cannot be subsequently inserted. This limits the choice of placement during surgery if the need arises.

Also, the above insert designs rely on a friction lock via contact between two simple surfaces. Simple surface friction locks are not reliable and come loose more easily than threaded locked holes. The result of such a design is inferior to that of the threaded plate and screw designs discussed below.

In U.S. Pat. No. 5,002,544, there is shown an osteosynthetic pressure plate having a cross-section transverse to the longitudinal axis of the plate at least at one point being wider toward the upper surface than toward the lower surface and the plate having recesses in the lower surface so that upon application to a bone there is space between the bone and the plate. The cross-section between the screw holes is reduced, preferably to the extent that the resistance of the plate to bending in this area is less than in the area of the holes. Because of the reduced bend resistance between the holes, the plate can more easily be adapted to conform to the anatomy of the bone. Furthermore, this can be done without deformation of the holes, thus minimizing the resulting loss of fatigue strength and minimizing the misfit of the screw heads.

Further, U.S. Pat. No. 5,709,686 describes a bone plate that has recesses or reduced thickness portions on its sides, between threaded apertures. Although the purpose is not specifically described, these recesses appear to function to avoid warpage of the threaded portions when the bone plate is bent. However, when such a bone plate is fixed to a bone, these discontinuous recesses are exposed and may potentially come into contact with and potentially aggravate muscle tissue.

Still further, U.S. Pat. No. 5,733,287 shows, in FIG. 4, a plate that has transverse cuts 13 and a longitudinal cut 14 on the lower surface 7 to reduce contact between the plate and bone. Due to the transverse undercuts 13, the cross-section 15 between the holes is already significantly reduced and therefore is not further decreased by an additional groove 10 on the upper surface 6 as in the embodiment according to FIG. 3. To avoid a cross-section that is too thin, the groove 10 on the upper surface 6 is made discontinuous in short segmental grooves 16 providing a smooth transition into and out of the holes 8.

In yet another solution, PCT application no. WO01/54601 combines the features of the DCS system discussed above with a locking screw. Such a system is known as the combi-slot. In this design, the stepped surface of the slot is generally ramped or tapered so as to be deeper at one end than at another. This enables the positioning and selective fixing of the bone plate for compressing two bone fragments together with a preload created by wedging action. In this manner, the bones are placed in a position that the surgeon believes would best promote healing.

Further, this combi-hole includes two distinct overlapping portions in a single slot. One portion of the slot is suited to receive a standard bone screw, while the other portion of the slot is suited to receive a threaded peg oriented perpendicular to the top surface of the bone plate. Also, the combi-holes are generally oriented with the threaded portions being on the innermost end of the combination and the unthreaded portions oriented toward the ends of the bone plate. This improvement increased the flexibility of choice available to orthopedic surgeons using the device in that it was more likely that a hole would be present at a suitable anchoring point in the bone plate. Nevertheless, there are often trauma situations that are best served by the threaded portion being at the extreme ends of the bone plate and/or at various positions throughout the plate. In addition, sometimes there is no specific center of the facture—in such a situation; use of the combi-hole design is limited. The combi-hole if further limited in that it allows the fixing of a screw in either the slotted portion or the threaded portion, but not both.

While patent application no. WO01/54601 has proven advantageous because screws can be locked to the plate; the presence of an unthreaded slot limits the user's ability to have multiple orientations for the screw.

In a further development, the AO Institute has studied and proposed the use of endpegs which are rigidly fixed in the extreme ends of the bone plate. Such an arrangement has been shown to better resist the flexing of the bone than use of a bone screw alone. Flexing can otherwise loosen the connection between the bone plate and bone in other bone plate systems.

U.S. Pat. No. 5,324,290 shows a complex bone plate having slots with countersunk circular recessed cuts at intervals along the slot (a similar arrangement is shown in U.S. Pat. No. 4,696,290). It further shows the bone plate torqued against the bone so as to at least marginally conform to the shape of the bone (see FIG. 2). Other patents of interest include U.S. Pat.

Nos. 3,716,050; 3,659,595; 5,681,311; 5,261,910, and 5,364,399, as well as German Patent application DE4341980A1, all showing combinations of conventional slots and recesses which do not fully accommodate a bone screw having a threaded head. In comparison with the combi-hole design and the friction locking design described above, what is needed is a bone plate that provides greater flexibility of choice to the surgeon. More specifically, what is needed is a bone plate that provides this choice of plate placement while reliably and permanently fixing the bone plate to the bone fragments, in any hole position.

What is needed is a bone plate that provides greater flexibility of choice to the surgeon, in a bone plate that has multiple orientations for the locking screw and thus, plate placement, while reliably and permanently fixing the bone plate to the bone fragments, in any hole position.

In addition, what is needed is a versatile bone plate having recesses which determine where the bone plate will bend, in order to avoid the threads in any holes to be bent or warped, while maintaining a smooth external surface.

Finally, what is needed is a bone plate with holes that create bidirectional compression.

SUMMARY OF THE INVENTION

The present invention relates to bone plates of complex form for use with bone screws having a head radius r. The bone plates have a main longitudinal axis, a bone-contacting bottom side and a top side with a plurality of bone screw apertures. At least one pair of the bone screw apertures forms an adjoined aperture pair. An adjoined aperture pair is defined in the figures and includes an additional relief-space contiguous to the open space of the apertures themselves. An adjoined aperture pair has a center-to-center distance d of the apertures along an axis running through the centers of the apertures. The center-to-center distance d is equal to or greater than the sum of the radii (r1+r2) of the individual bone screw heads used with the aperture pair. The adjoined pair of screw apertures is further defined by the above noted. relief-space (or bar-space feature) disposed between and joining them, to provide a complex aperture, the opening of which gives the complex aperture a "bar-bell" like configuration. Preferably, the additional relief-space feature is configured as either a straight slot, or as a constricted or "waisted" slot centered on the axis joining the opening of the screw apertures. When applied to a bone, two different adjoined aperture pairs are located so as to lie on opposite sides of an osteotomy site. The installation configuration of bone screws in the complex bone plate is selectable, depending on the physiology of the bone being repaired.

An object of the invention is to provide a surgeon with the option of placing two bone screws in adjacent positions so that the heads of the adjacent bone screws can abut without overlapping. Another object of the invention is to provide an orthopedic surgeon greater flexibility of choice in that a threaded peg or screw providing secure fixing can be positioned at any interval along the bone plate, including at its extreme ends or on its elbow.

BRIEF DESCRIPTION OF THE DRAWINGS

FIG. 4 is a side view of an exemplary assembly of the screws and bone plate of the present invention.

FIG. 5 is a schematic illustration of the present bone plate fixed to a bone.

DETAILED DESCRIPTION OF THE PREFERRED EMBODIMENTS

Figure 1A:
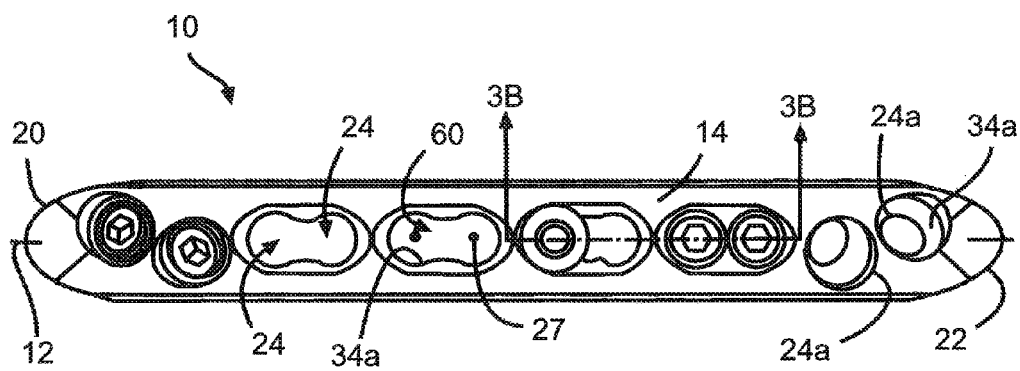
FIGS. 1A and 1B respectively are top views of a bone plate of the invention incorporating one type of relief-space, and a close-up view of the first end of the bone plate.

Referring now to the drawings, the details of preferred embodiments of the present invention are graphically and schematically illustrated. Like elements in the drawings are represented by like numbers, and any similar elements are represented by like numbers with a different lower case letter suffix.

Figure 1B:
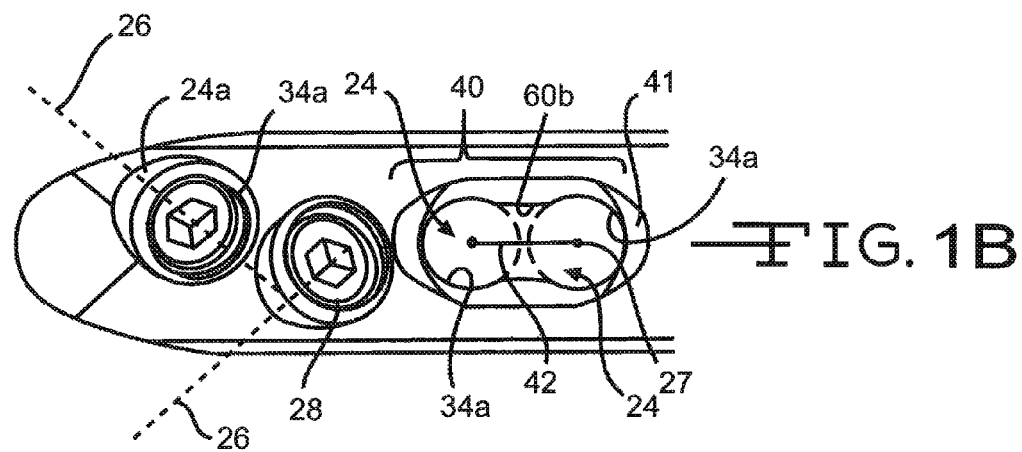
Figure 2A:
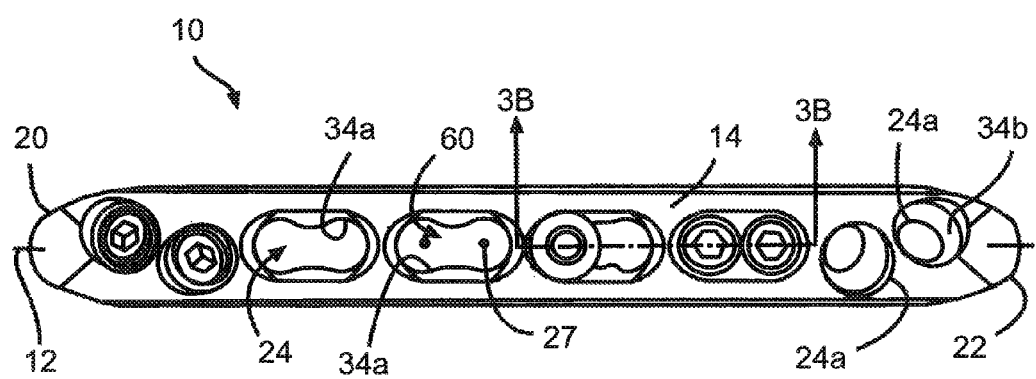
FIGS. 2A and 2B respectively are top views of a bone plate of the invention incorporating an alternative type of relief-space, and a close-up view of the first end of the bone plate.

As exemplified in FIGS. 1A and 2A, the present bone plate 10 has a main longitudinal axis 12, a bone-contacting bottom side 16 (see FIG. 4), a top side 14 and opposite first 20 and second 22 plate ends. A series of screw apertures 24 extending from the top side 14 of the plate 10 through to its bottom side 16 are formed along the plate axis 12. The screw apertures 24 serve as bone screw guides through which points bone screws 28 are inserted into underlying bone to anchor the bone plate 10 to different parts or fragments 80 of a bone to be reinforced by the bone plate 10 (see FIG. 5). The screw apertures 24 have a screw axis 26 through its center 27 (the general path that a screw takes when inserted through the aperture) which is either perpendicular or angled (see FIGS. 1B and 2B) relative to the plane of the bone plate 10 in the vicinity of the screw aperture 24 depending on the need of a particular application or surgical protocol.

Figure 2B:
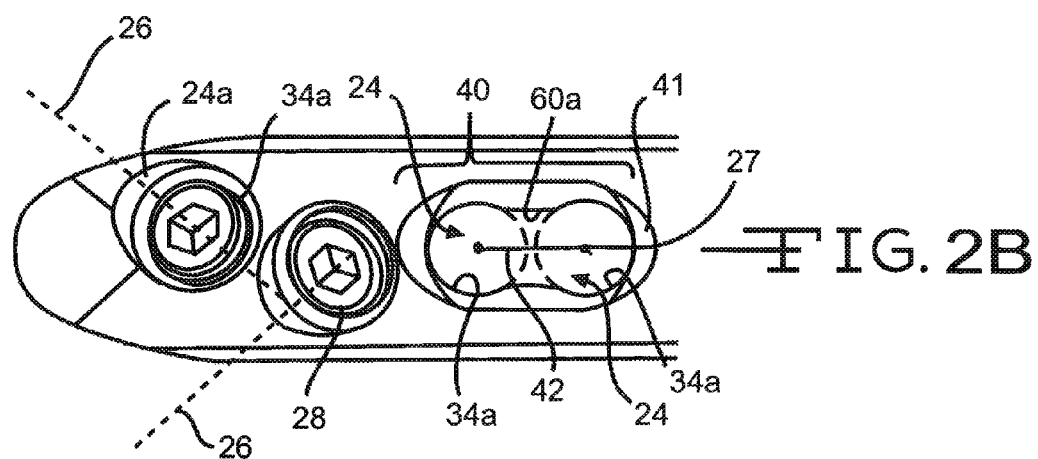

Additionally, the bone plate 10 of the present invention has one or more complex apertures 40 which comprise a pair of closely spaced apart screw apertures 24 adjoined by a "relief"-space feature 60. The relief-space feature 60 is disposed between and joining the openings of the two pair of closely spaced apart screw apertures 24 to provide a complex aperture having a single opening which has a "dumb-bell" or "bar-bell" like configuration. Preferably, the relief-space 60 is configured. as either a straight slot 60a or a constricted or "waisted" slot 60b. The relief-space is centered on the radial axis 42 joining the opening of the screw apertures 24. As noted above, the bone plate 10 has at least one complex screw aperture 40 made up of two threaded-seat apertures 34a joined by a relief-space 60. However, multiplex screw apertures (not shown) made up of more than two screw apertures 24 are anticipated, but at least one pair of the screw apertures 24 is separated by a relief-space 60. in the preferred embodiment of FIGS. IA and IB, the relief-space 60 is a constricted or "waisted" relief 60b. Referring to FIG. 1B, a constricted or waisted relief 60b is a relief-space 60 defined between the pair of closely spaced apart screw apertures 24 by two facing arcuate walls which have their cord parallel to the radial axis 42 of the closely spaced apertures 24b. The relief-space 60 in the alternative preferred embodiment of FIGS. 2A and 2B is a straight-slot relief 60a. A straight-slot relief is defined between the pair of closely spaced apart screw apertures 34a by two facing parallel walls.

Figure 6A:
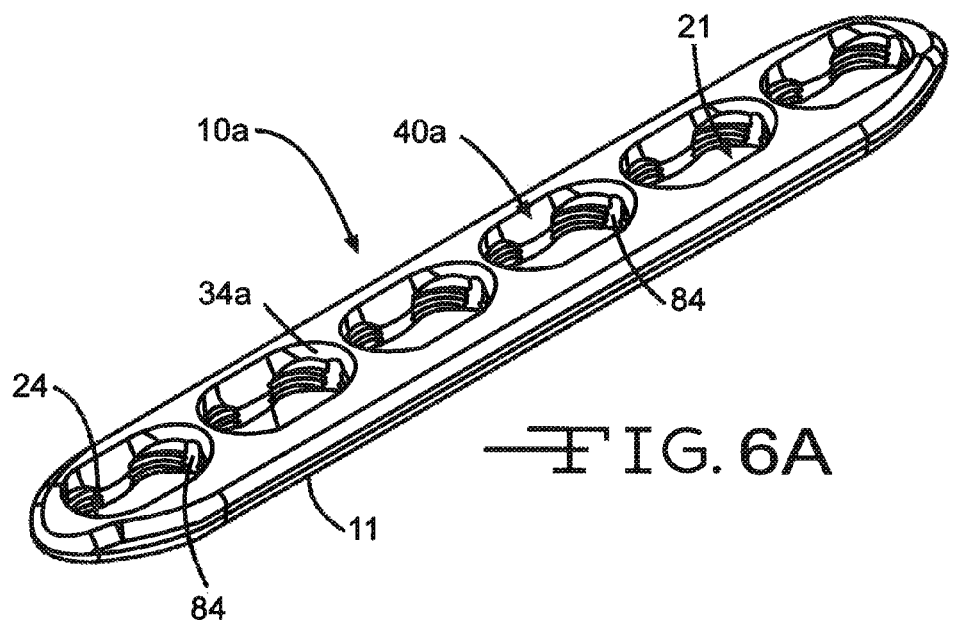
FIGS. 6A and 6B are top-side perspectives views of an alternative embodiment of the present bone plate showing (A) the full plate and (B) a detailed partial view.
Figure 6B:
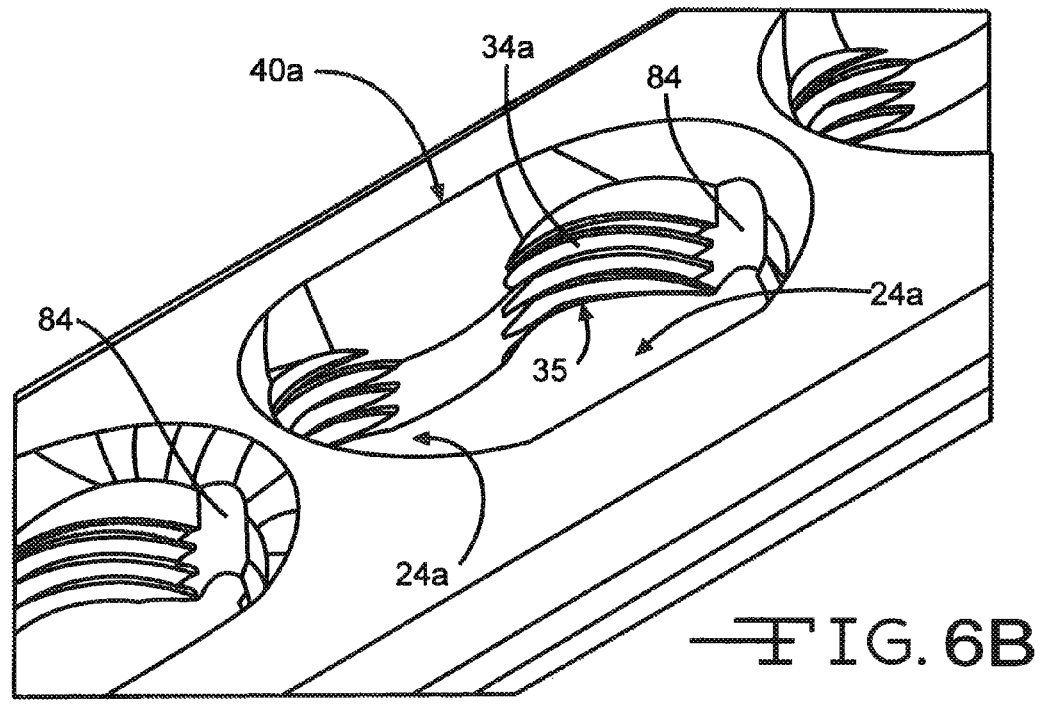
Figure 6C:
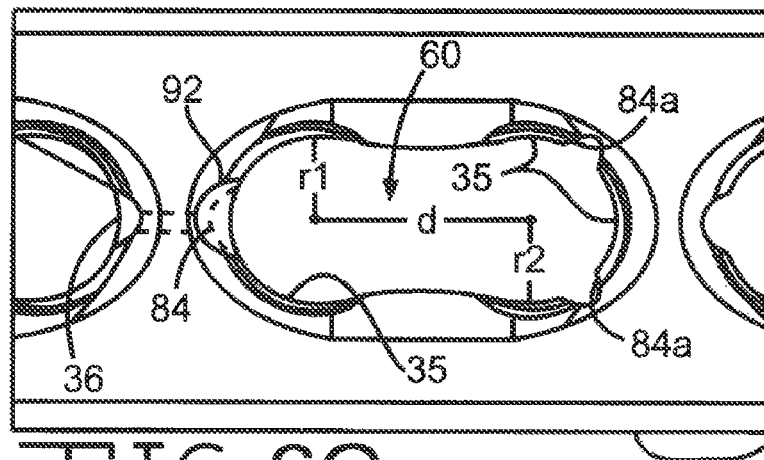
FIGS. 6C and 6D respectively are top-side and bottom-side plan views detaining respective portions of the present bone plate.
Figure 6D:
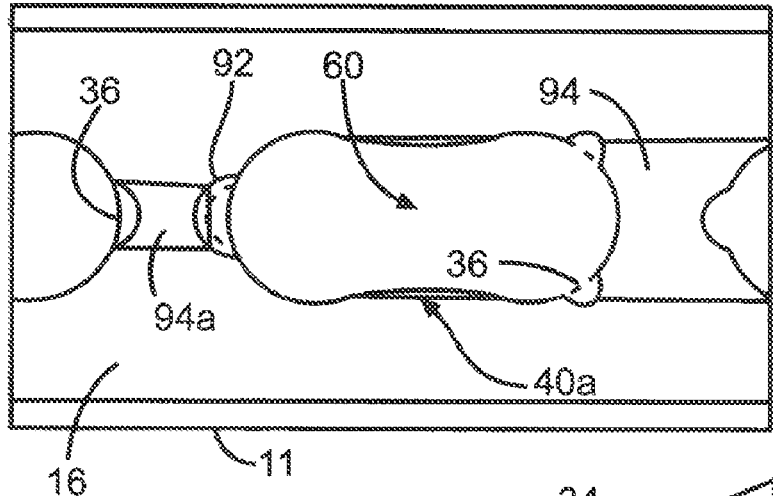
Figure 6E:
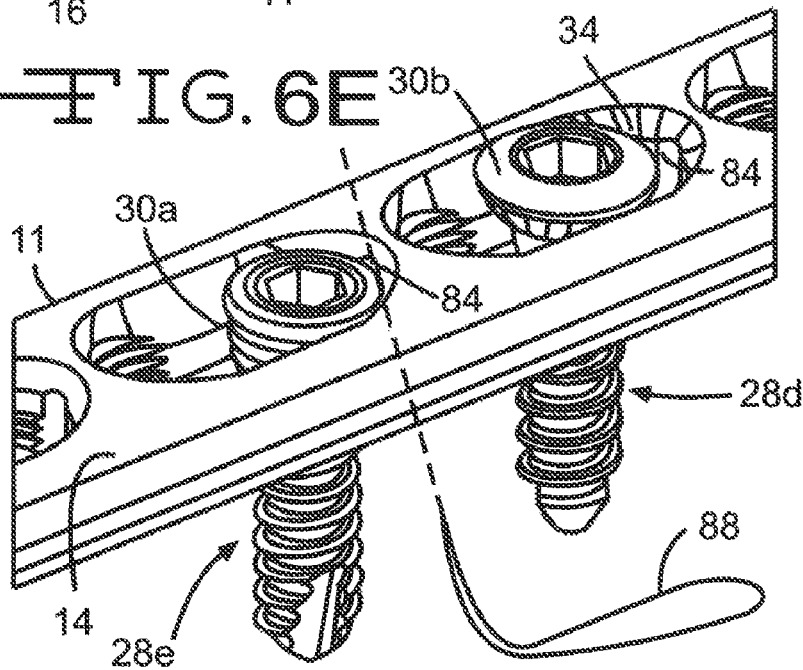
FIG. 6E is atop-side perspective view of a portion of the present bone plate with bone screws inserted into two of the complex apertures.

A complex-aperture 40 preferably has wide bevels 41 on a far and near end with respect to the plate axis 12, and has defined multifaceted head-seats 34 (e.g., see FIG. 6E). Examples of multifaceted head-seats features include: threaded surfaces, ringed surfaces and a tapered lead-in surface formed on at least the top side 14 of the elongated plate 11. A tapered lead-in surface can also be either an elongated chamfer as illustrated in the figures.

Additionally, the present bone plate 10 includes angled screw apertures 24a. Referring now to FIGS. 1B and 2B, two angled apertures 24a (preferably positioned proximate at least one of the plate ends 20, 22 of the bone plate 10) have screw axes 26 that are angled from the perpendicular relative to the plane of the bottom side 16 of the bone plate 10, and preferably in opposing orientations. The orientation is selectable by one of skill in the field to provide an optimal utility for a variety of operative procedures. In this particular embodiment, the angled holes 24a in the plate ends 20, 22 are inclined at an angle of approximately forty-five degrees relative to the plane of the bottom side 16 of the bone plate 10. The angled apertures 24a are disposed relative to each other to accept and to guide a bone screw 28 at opposing angles in order to securely anchor the bone plate 10 to the bone fragment 80 (see FIG. 5).

It should be noted that screw apertures 24 can be configured to be complementary to bone screws 28 having a number of configurations of screw heads 30 and shanks 32. For example, as exemplified in FIGS. 3A and 3B, a bone screw 28 can have a threaded-head 30a or an unthreaded-head 30b. Additionally, a bone screw 28 with a threaded-head 30a can have a threaded-shank 32a. or an unthreaded-shank 32b (see FIG. 7). Correspondingly, the screw apertures 24 can have head-seat 34 for receiving a bone screw 28 that is a threaded-seat 34a or an unthreaded-seat 34b to respectively receive a bone screw 28 having a threaded-head 30a or an unthreaded-head 30b. The bone plate 10 may optionally use a locking bone peg 50, i.e., a bone screw 28 with a threaded-head 30a and unthreaded-shank 32b (see FIG. 7). Preferably, the threads cut in the head of the bone pegs 50 are designed so as to lock with the threaded apertures 34a in order to better ensure rigid fixing of a fracture. The locking feature used can be any of the known methods of locking threads by mechanical means.

Figure 3A:
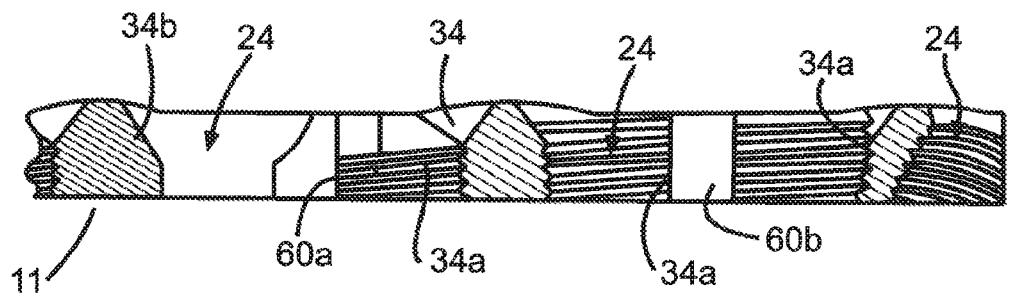
FIGS. 3A and 3B are cross-sectional side views of a section of the bone plate of FIGS. 1A and 2A taken along line 3-3, and illustrating locations for the relief-space.
Figure 3B:
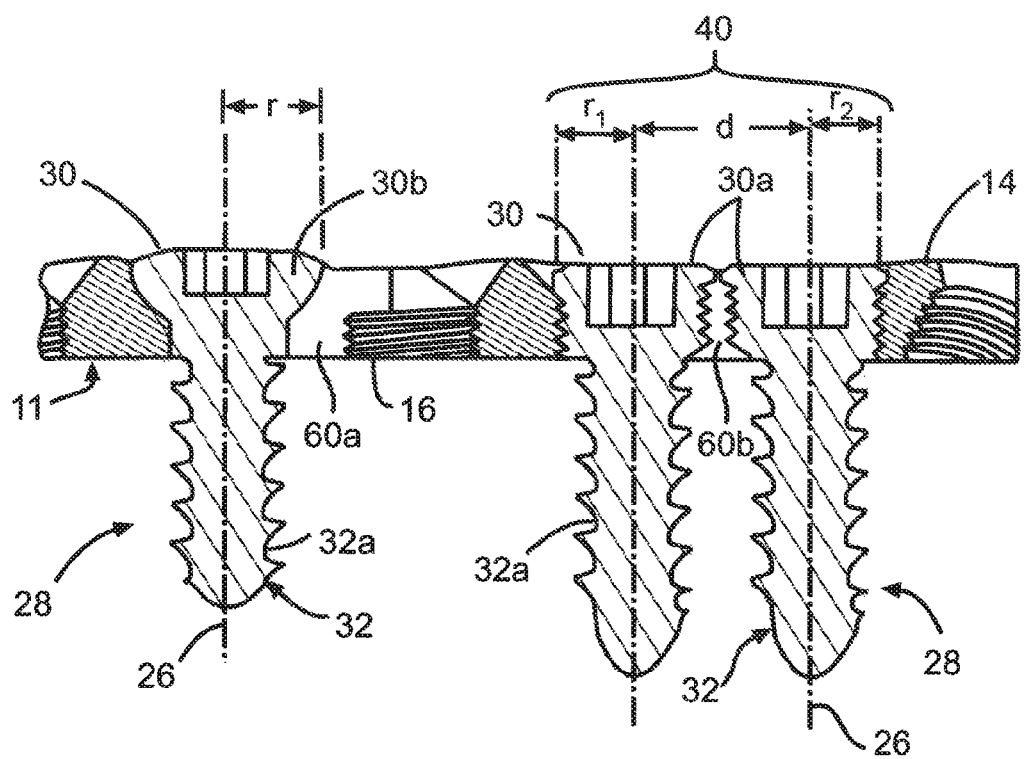

Referring now to FIGS. 3B and 6C, the center-to-center distance d of the two screw apertures 24 of the duplex-aperture 40 corresponds substantially to the sum of the radii of the of the two screw apertures 24b, i.e., r1+r2=d. This configuration enables installation of bone screws 28 through the elongated plate 11 so that the heads 32 of the bone screws 28 can be positioned as close together as possible, and even to be touching.

In the embodiment illustrated in FIG. 4, a pair of angled screw apertures 24a is shown at the first plate end 20 of a bone plate 10 with bone screws 28 installed through them. In this embodiment, the screw axes 26 of the angled screw apertures 24a at the first plate end 20 slant toward the second plate end 22. The general triangular configuration formed by the bone screw axes 26a, 26b with the axis 12 of the elongated plate 11 creates a triangular truss-like structure that is able to resist a wide range of forces which could otherwise tend to loosen an installed bone plate 10. Consequently, this configuration resists pull-out forces coming from a wider range of directions. Although FIG. 4 shows the screw axes 26 of the angled screw apertures 24a at the first plate end 20 slant toward the second plate end 22, they can slant in the opposite direction as shown in FIGS. 1B and 2S. Additionally, the screw apertures 24 proximate the plate ends 20, 22 are independent of screw apertures 24 located in the mid-section of the bone plate 10. It should be noted that in other preferred embodiments, a pair of angled screw apertures 24a can be disposed at both first and second plate ends 20, 22 of a bone plate 10 (see FIGS. 1A and 2A), or at any other location on the elongated plate 11.

Referring now to FIG. 5, in another embodiment, the bone plate 10 is particularly suited for femoral osteotomies 44, correcting medial patellar luxations, and/or other corrective osteotomies of the femur. The bone plate 10 has a main longitudinal axis 12, a bone contacting bottom side 16 and a top side 14 with one or more complex apertures 40 having a pair of closely adjacent screw apertures 24, which communicate through the plate 11 from the top side 14 to the bottom side 16. The closely adjacent pairs of screw apertures 24 have a multifaceted screw head surface 34 (FIGS. 3A and 6E). Preferably, when the elongated plate 11 is applied to a bone 80, two complex apertures 40 are disposed to lie on opposite sides 51 of an osteotomy site 44. In the figure shown, the bone plate 10 also has two pairs of angled apertures 24a. The pairs of screw apertures 24 can act together as compression fittings. When applied to a bone part 80, each pair of screw apertures 24 can be disposed to lie on opposite sides 51 of an osteotomy site 44.

An alternative embodiment of the present bone plate 10a is illustrated in FIGS. 6A to 6E. In this embodiment the complex apertures 40a are similar to the complex apertures described above, but differ in that they have a relief notch 84 disposed in the screw head seat 34 portion of one or both screw apertures 24. The relief notch 84 provides desirable advantages that are not similarly accomplished in their absence. For example, as shown in FIG. 6C, a self-locking insert 92 can be disposed in the notch 84 to provide increased friction for setting a. threaded head bone screw 30a set in a threaded aperture 24a. As also illustrated in FIG. 6C, it is intended that a screw aperture 24 may have more than one relief notch 84a. A further example of an advantage of the present notch feature is illustrated in FIG. 6E, which illustrates that a tensioning wire 88 may be looped around a first bone screw 28d, passed along the bottom side 16 of the elongated plate 11 and the ends of the wire drawn up to the top side 14 of the elongated plate 11 through the relief notch 84 in an adjacent second bone screw 28e. In the embodiment illustrated in FIG. 6D, the bottom-side 16 of the elongated plate 11 is provided with a clearance channel 94, 94a recessed into the surface of the bottom-side of the plate 11. The clearance channel communicates with the relief notch 84 to provide a path for the tensioning wire 88 to be easily removed through the relief notch 84 after the bone screws 28 have been set against the bone plate 10a.

The notch feature 84 defines a screw aperture 24 having threaded screw head seat 34a with at least one threaded surface portion 35 and one unthreaded surface portion 35a. In a complex aperture 40a, the notch feature 84 defines a screw aperture 24 in which the threaded screw head seat 34a has at least two threaded surface portions 35 and two unthreaded surface portions 36, with one of the at least two unthreaded surface portions being the relief zone 60.

Figure 7:
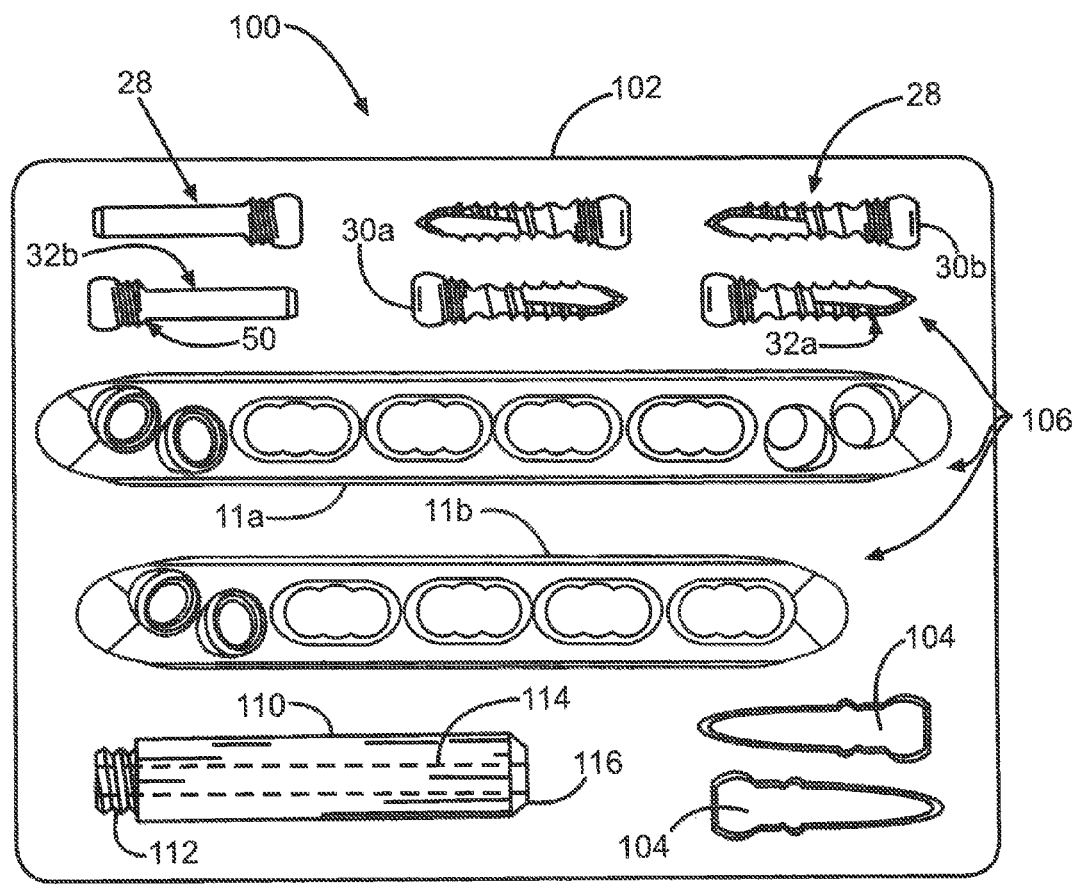
FIG. 7 is a top view of a kit of the present invention.

Referring now to FIG. 7, another embodiment includes an orthopedic bone plate kit 100 which includes a compartmented container 102, preferably having shaped compartment spaces 104 corresponding to the shape of the kit item 106 to be received in the shaped compartment space 104. Kit items 106 contained in the kit 100 include one or more bone plates 10 having the same or similar elongated plate features

11a and 11b, and a plurality of bone screws 28. Note that the bone screws 28 may be of a variety of somewhat different configurations practicable with the screw apertures 24 of the present invention. As examples, included in the kit 100 shown area threaded-head bone screws 30a, unthreaded-head bone screws 30b (both with threaded shanks) and threaded-head pegs 32b (i.e., an unthreaded shank), all can be of various lengths. Additionally shown in the kit 100 is a drill guide 110. The drill guide 110 has a threaded end 112 that can screw into the threaded-seat 34a on a screw aperture 24. The drill guide has a hollow bore 114 that serves as a guide for a drill bit (not shown) for use to drill a pilot hole in the bone for the bone screw 28 that is to be inserted into the bone through the screw aperture 24.

In an advantage, unlike the case with overlapping threaded screw apertures (i.e., their center-to-center distance being less than d), a surgeon is able to place two bone screws 28 side by side, in a very close proximate position abutting one another.

In another advantage, the invention enables the spacing between bone screws that is so close that the surgeon is able to maintain a standard spacing such as that purveyed by the AO Institute, founded by Synthes S.A.

In another advantage, where a fracture runs between screw apertures 24, a surgeon is able to place two bone screws 28 on opposite sides of the fracture, thereby better fixing the broken bone parts 80 together for optimal healing.

In an advantage of the invention, the bone plate 10 provides greater flexibility of choice to the surgeon in that a threaded-head peg 50 providing secure fixing can be positioned at any interval along the elongated plate 11, including at its extreme ends.

In another advantage, the bone plate 10 provides greater flexibility of choice by providing multiple complex apertures 40 oriented either along the longitudinal axis 12 of the elongated plate 11, oriented at an angle to the longitudinal axis 12, and staggered along the axis 12.

In still another advantage, the threaded head apertures 34a of the elongated plate 11 are provided with threads cut for a screw axis 26 perpendicular to the top side 14 of the elongated plate 11, as well as for a screw axis 26 at a non-perpendicular angle to the top side 14 of the elongated plate 11.

The configuration of this complex bone plate 10 may vary, depending on the physiology of the patient. An illustration of the flexibility of application of the plate 80 is its flexible use in osteotomy.

Multiple variations and modifications are possible in the embodiments of the invention described here. Although certain illustrative embodiments of the invention have been shown and described here, a wide range of modifications, changes, and substitutions is contemplated in the foregoing disclosure. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

What is claimed is:

1. A bone plate, comprising:
    a) an elongated plate having a longitudinal axis, a bone contacting bottom side, a top side, a thickness between the bottom and top sides with at least one complex screw aperture extending through the plate thickness and comprised of a first screw aperture and an aligned second screw aperture adjoined by a relief zone disposed between the first and second screw apertures;
    b) wherein the first screw aperture of the at least one complex aperture has a first radius measured from a first center of a first seat thereof and the second screw aperture has a second radius measured from a second center of a second seat thereof, and
    c) wherein each of the first and second apertures of the at least one complex aperture comprises a beveled upper surface extending from the top side of the plate downwardly and inwardly part way through the plate thickness to a lower, threaded seat portion extending from where the beveled surface ends to the bottom side of the bone plate, and
    d) wherein the at least one complex aperture has a complex aperture distance measured from the center of the first radii to the center of the second radii along the aligned first and second radii and the relief zone disposed between the adjoined first and second screw apertures that is at least equal to a sum of the first and second radii, and
    e) wherein the relief zone adjoining the first and second apertures is defined by two opposed unthreaded surfaces, each of the two opposed unthreaded surfaces forming an upper unthreaded inclined ramp extending from the top side downwardly and inwardly at least part way through the plate thickness to an unthreaded lower portion having opposed planar surfaces aligned parallel to each other and extending to the bottom side, and
    f) wherein the two opposed planar surfaces of the relief zone are aligned parallel to, but spaced from the aligned first and second radii by a lateral distance that is less than twice the distance of the first radii and less than twice the distance of the second radii.

2. The bone plate of claim 1 wherein at least one of the first and second screw apertures has a head-seat that is selected from the group consisting of:
    a) a threaded head seat,
    b) a ringed surface seat,
    c) a ridged surface seat, and
    d) a tapered lead-in surface seat in combination with at least one of a threaded head seat, a ringed surface seat, and a ridged surface seat.

3. The bone plate of claim 1 wherein the first screw aperture or the second screw aperture of the at least one complex aperture has at least one relief notch set into its beveled upper surface.

4. The bone plate of claim 1, wherein the first screw aperture or the second screw aperture of the at least one complex aperture has at least one relief notch set into its beveled upper surface and a self-locking insert retained in the at least one relief notch.

5. A method of installing a bone plate in situ to fix a spatial relationship of at least two bone parts of a bone, the method comprising the steps of:
    a) providing the bone plate of claim 1;
    b) positioning the bone plate over the bone with the relief zone positioned over a bone surface feature to which it is to be fixed; and
    c) installing a first threaded head bone screw in either the first or the second threaded screw apertures of the at least one complex aperture to anchor the bone plate to one of the at least two bone parts;
    d) followed by installing a second bone screw in another screw aperture of the bone plate of the bone plate to thereby anchor the bone plate to the two bone parts.

6. An orthopedic kit comprising:
a) a compartmented container having compartment spaces that contain a first item being at least one bone plate according to claim 1; and
b) a second item of the kit being a plurality of bone screws with threaded heads and unthreaded heads.

7. A bone plate, comprising:
a) an elongated plate having a longitudinal axis, a bone contacting bottom side, a top side, a thickness between the bottom and top sides with at least one complex screw aperture extending through the plate thickness and comprised of a first screw aperture and an aligned second screw aperture adjoined by a relief zone disposed between the first and second screw apertures;
b) wherein the first screw aperture of the at least one complex aperture has a first radius measured from a first center of a first seat thereof and the second screw aperture has a second radius measured from a second center of a second seat thereof, and
c) wherein each of the first and second apertures of the at least one complex aperture comprises a beveled upper surface extending from the top side of the plate downwardly and inwardly part way through the plate thickness to a lower, threaded seat portion extending from where the beveled surface ends to the bottom side of the bone plate, and
d) wherein the at least one complex aperture has a complex aperture distance measured from the center of the first radii to the center of the second radii along the aligned first and second radii and the relief zone disposed between the adjoined first and second screw apertures that is at least equal to a sum of the first and second radii, and
e) wherein the relief zone adjoining the first and second apertures is defined by two opposed unthreaded surfaces, each of the two opposed unthreaded surfaces forming an upper unthreaded inclined ramp extending from the top side downwardly and inwardly at least part way through the plate thickness to an unthreaded lower portion having opposed planar surfaces aligned parallel to each other and extending to the bottom side, and
f) wherein the two opposed planar surfaces of the relief zone are aligned parallel to, but spaced from the aligned first and second radii by a lateral distance that is less than twice the distance of the first radii and less than twice the distance of the second radii.

8. The bone plate of claim 7 wherein at least one of the first and second radii of the respective first and second screw apertures extend into the relief-zone.

9. The bone plate of claim 7 wherein at least one of the first and second screw apertures has a head-seat that is selected from the group consisting of:
a) a threaded head seat,
b) a ringed surface seat,
c) a ridged surface seat, and
d) a tapered lead-in surface seat in combination with a threaded head seat, a ringed surface seat, and a ridged surface seat.

10. The bone plate of claim 7 wherein the beveled upper surface of at least one of the first and second screw apertures is a threaded surface portion.

11. The bone plate of claim 7 wherein the first screw aperture or the second screw aperture of the at least one complex aperture has at least one relief notch set into its beveled upper surface.

12. The bone plate of claim 7 wherein the first screw aperture or the second screw aperture of the at least one complex aperture has at least one relief notch set into its beveled upper surface and a self-locking insert retained in the at least one relief notch.

13. The bone plate of claim 7 wherein the first screw aperture is configured to receive a first bone screw and the second screw aperture is configured to receive a second bone screw such that the first bone screw contacts the second bone screw.

14. The bone plate of claim 7 wherein the respective beveled surfaces of the first and second screw apertures extend downwardly and inwardly from the upper surface to the lower threaded surface at either the same or different angles.

15. The bone plate of claim 7 wherein the at least one complex aperture is adapted to receive:
a) a single threaded head bone screw in the first or second screw apertures to anchor the elongated plate to a bone part; and
b) two threaded head bone screws, the first of the two threaded head bone screws being positionable in the first screw aperture and the second threaded head bone screw being positionable in the second screw aperture so the first threaded head bone screw and the second threaded head bone screw have their respective threaded heads close to each other when properly positioned to anchor the elongated plate to the bone part.

16. A bone plate, comprising:
a) an elongated plate having a longitudinal axis, a bone contacting bottom side with a recessed clearance channel disposed along the axis, a top side, a thickness between the bottom and top sides with at least one complex aperture extending through the plate thickness and comprised of a first screw aperture and a second screw aperture adjoined by a relief zone disposed between the first and second screw apertures;
b) wherein the first screw aperture of the at least one complex aperture has a first radius measured from a first center of a first seat thereof and the second screw aperture has a second radius measured from a second center of a second seat thereof, and
c) wherein each of the first and second apertures of the at least one complex aperture comprises a beveled upper surface extending from the top side of the plate downwardly and inwardly part way through the plate thickness to a lower, threaded seat portion extending from where the beveled surface ends to the bottom side of the bone plate, and;
d) wherein the relief-zone adjoining the first and second screw apertures is defined by two opposed unthreaded surfaces, each of the two opposed unthreaded surfaces forming an upper unthreaded inclined ramp extending from the top side downwardly and inwardly at least part way through the plate thickness to an unthreaded lower portion having opposed planar surfaces aligned parallel to each other and extending to the bottom side, and
e) wherein the at least one complex aperture has a complex aperture distance measured from the center of the first radii to the center of the second radii along the parallel first and second radii and the relief zone disposed between the adjoined first and second screw apertures that is at least equal to a sum of the first and second radii, and
f) wherein the two opposed unthreaded surfaces of the relief zone are spaced apart by a lateral distance that is less than twice the distance of the first radii and less than twice the distance of the second radii; and g) wherein the at least one complex aperture has the relief zone disposed between the first screw aperture and the second screw aperture.

17. The bone plate of claim 16 wherein the first screw aperture or the second screw aperture of the at least one complex aperture has at least one relief notch set into its beveled upper surface.

18. A bone plate having a thickness extending from a bone-contacting bottom side to a top side with at least two complex apertures extending through the plate thickness, each complex aperture comprised of a first screw aperture and a second screw aperture adjoined by a relief-space,
   a) wherein the first screw aperture of one of the at least two complex apertures has a first radius measured from a first center of a first seat thereof and the second screw aperture of the one of the at least two complex apertures has a second radius measured from a second center of a second seat thereof, and
   b) wherein each of the first and second apertures of the one of the at least two complex apertures comprises a beveled upper surface extending from the top side of the plate downwardly and inwardly part way through the plate thickness to a lower, threaded seat portion extending from where the beveled surface ends to the bottom side of the bone plate, and
   c) wherein the relief zone adjoining the first and second apertures of the one of the at least two complex apertures is defined by two opposed unthreaded surfaces, each of the two opposed unthreaded surfaces forming an unthreaded inclined ramp extending from the top side downwardly and inwardly at least part way through the plate thickness to an unthreaded lower portion having opposed planar surfaces aligned parallel to each other and extending to the bottom side, and
   d) wherein the one of the at least two complex apertures has a complex aperture distance measured from the center of the first radii to the center of the second radii along the parallel first and second radii and the relief zone disposed between the adjoined first and second screw apertures that is at least equal to a sum of the first and second radii, and
   e) wherein the two opposed unthreaded surfaces of the relief zone are spaced apart by a lateral distance that is less than twice the distance of the first radii and less than twice the distance of the second radii,
   f) wherein the lower, threaded seat portion of the first screw aperture, the unthreaded lower portion of the relief zone and the lower, threaded seat portion of the second screw aperture provide a bar-bell shape extending from where the beveled upper surfaces of the respective first and second screw apertures and the upper unthreaded inclined ramp of the relief zone end at the bar-bell shape to the bottom side of the bone plate,
   g) the first threaded lower portion of the first screw aperture and the second threaded lower portion of the second screw aperture each being adapted to lock with threads of a corresponding bone screw; and
   h) the unthreaded lower portion of the relief zone being adapted to receive a corresponding bone screw.

19. A bone plate having a thickness extending from a bone-contacting bottom side to a top side with at least one complex aperture extending through the plate thickness, the at least one complex aperture comprised of a first screw aperture and a second screw aperture adjoined by a relief-space,
   a) wherein the first screw aperture of the at least one complex aperture has a first radius measured from a first center of a first seat thereof and the second screw aperture of the at least one complex aperture has a second radius measured from a second center of a second seat thereof, and
   b) wherein each of the first and second screw apertures of the at least one complex aperture comprises a beveled upper surface extending from the top side of the plate downwardly and inwardly part way through the plate thickness to a lower, threaded seat portion extending from where the beveled surface ends to the bottom side of the bone plate, and
   c) wherein the relief zone adjoining the first and second screw apertures of the at least one complex aperture is defined by two opposed unthreaded surfaces, each of the two opposed unthreaded surfaces forming an unthreaded inclined ramp extending from the top side downwardly and inwardly at least part way through the plate thickness to an unthreaded lower portion having opposed planar surfaces aligned parallel to each other and extending to the bottom side, and
   d) wherein the at least one complex aperture has a complex aperture distance measured from the center of the first radii to the center of the second radii along the parallel first and second radii and the relief zone disposed between the adjoined first and second screw apertures that is at least equal to a sum of the first and second radii, and
   e) wherein the two opposed unthreaded surfaces of the relief zone are spaced apart by a lateral distance that is less than twice the distance of the first radii and less than twice the distance of the second radii,
   f) wherein the first screw aperture and the second screw aperture have an offset of a given distance between their respective first and second centers thereof, and the first and second centers are staggered about a longitudinal axis of the bone plate;
   g) wherein the lower, threaded seat portion of the first screw aperture, the unthreaded lower portion of the relief zone and the lower, threaded seat portion of second screw aperture provide a bar-bell shape extending from where the beveled upper surfaces of the respective first and second screw apertures and the upper unthreaded inclined ramp of the relief zone end at the bar-bell shape to the bottom side of the bone plate,
   h) the first threaded lower portion of the first screw aperture and the second threaded lower portion of the second screw aperture each being adapted to lock with threads of a corresponding bone screw; and
   i) the unthreaded lower portion of the relief zone being adapted to receive a corresponding bone screw.

20. A bone plate having a thickness extending from a bone-contacting bottom side to a top side with at least one complex aperture extending through the plate thickness, the at least one complex aperture comprised of a first screw aperture and a second screw aperture adjoined by a relief-space,
   a) wherein the first screw aperture of the at least one complex aperture has a first radius measured from a first center of a first seat thereof and the second screw aperture of the at least one complex aperture has a second radius measured from a second center of a second seat thereof, and
   b) wherein each of the first and second apertures of the at least one complex aperture comprises a beveled upper surface extending from the top side of the plate downwardly and inwardly part way through the plate thickness to a lower, threaded seat portion extending from where the beveled surface ends to the bottom side of the bone plate, and c) wherein the relief zone adjoining the first and second screw apertures of the at least one complex aperture is defined by two opposed unthreaded surfaces, each of the two unthreaded surfaces forming an unthreaded inclined ramp extending from the top side downwardly and inwardly at least part way through the plate thickness to an unthreaded lower portion having opposed planar surfaces aligned parallel to each other and extending to the bottom side, and d) wherein the at least one complex aperture has a complex aperture distance measured from the center of the first radii to the center of the second radii along the parallel first and second radii and the relief zone disposed between the adjoined first and second screw apertures that is at least equal to a sum of the first and second radii, and e) wherein the two opposed unthreaded surfaces of the relief zone are spaced apart by a lateral distance that is less than twice the distance of the first radii and less than twice the distance of the second radii, f) wherein the lower, threaded seat portion of the first screw aperture, the unthreaded lower portion of the relief zone and the lower, threaded seat portion of the second screw aperture provide a bar-bell shape extending from where the beveled upper surfaces of the respective first and second screw apertures and the upper unthreaded inclined ramp of the relief zone end at the bar-bell shape to the bottom side of the bone plate, g) the first threaded lower portion of the first screw aperture and the second threaded lower portion of the second screw aperture each being adapted to lock with threads of a corresponding bone screw; and h) the unthreaded lower portion of the relief zone being adapted to receive a corresponding bone screw.

21. A bone plate having a thickness extending from a bone-contacting bottom side to a top side with at least one complex aperture extending through the plate thickness, wherein the at least one complex aperture is comprised of an inclined ramp having an oval shape at the top side of the plate with the inclined ramp extending from the top side downwardly and inwardly part way through the plate thickness to a lower portion having a bar-bell shape, the bar-bell shape provided by a first screw aperture and a second screw aperture adjoined by a relief zone disposed between the first and second screw apertures, a) wherein the first screw aperture has a first radius measured from a first center thereof and the second screw aperture has a second radius measured from a second center thereof, and b) wherein the first and second screw apertures comprise a lower, threaded seat portion extending from where the inclined ramp ends to the bottom side of the bone plate, and c) wherein the relief zone adjoining the first and second screw apertures has an unthreaded lower portion having opposed planar surfaces aligned parallel to each other and extending to the bottom side, and d) wherein the at least one complex aperture has a complex aperture distance measured from the center of the first radii to the center of the second radii along the parallel first and second radii and the relief zone disposed between the adjoined first and second screw apertures that is at least equal to a sum of the first, and second radii, and e) wherein the two opposed planar surfaces of the relief zone are spaced apart by a lateral distance that is less than twice the distance of the first radii and less than twice the distance of the second radii.

22. A bone plate having a thickness extending from a bone-contacting bottom side to a top side with at least one complex aperture extending through the plate thickness, wherein the at least one complex aperture is comprised of an inclined ramp having an oval shape at the top side of the plate with the inclined ramp extending from the top side downwardly and inwardly part way through the plate thickness to a lower portion having a bar-bell shape, the bar-bell shape provided by a first screw aperture and a second screw aperture adjoined by a relief zone disposed between the first and second apertures, a) wherein the first screw aperture has a first radius measured from a first center thereof and the second screw aperture has a second radius measured from a second center thereof, and b) wherein the first and second screw apertures comprise a lower, threaded seat portion extending from where the inclined ramp ends to the bottom side of the bone plate, and c) wherein the relief zone adjoining the first and second screw apertures has an unthreaded lower portion having opposed planar surfaces aligned parallel to each other and extending to the bottom side, and d) wherein the at least one complex aperture has a complex aperture distance measured from the center of the first radii to the center of the second radii along the parallel first and second radii and the relief zone disposed between the adjoined first and second screw apertures that is greater than a sum of the first and second radii, and e) wherein the two opposed planar surfaces of the relief zone are spaced apart by a lateral distance that is less than twice the distance of the first radii and less than twice the distance of the second radii.

23. A bone plate, comprising:

a) an elongated plate having a longitudinal axis, a bone contacting bottom side, a top side, a thickness between the bottom and top sides with at least one complex screw aperture extending through the plate thickness and comprised of a first screw aperture and a second screw aperture adjoined by a relief zone disposed between the first and second screw apertures;

b) wherein the first screw aperture of the at least one complex aperture has a first radius measured from a first center of a first seat thereof and the second screw aperture has a second radius measured from a second center of a second seat thereof, and c) wherein each of the first and second screw apertures of the at least one complex aperture comprises a beveled upper surface extending from the top side of the plate downwardly and inwardly part way through the plate thickness to a wall surface that, in turn, extends downwardly to a lower, threaded seat portion extending from where the wall surface ends to the bottom side of the bone plate, and d) wherein the relief zone adjoining the first and second screw apertures is defined by two opposed unthreaded surfaces, each of the two opposed unthreaded surfaces forming an upper unthreaded inclined ramp extending from the top side downwardly and inwardly at least part way through the plate thickness to an unthreaded lower portion having opposed planar surfaces aligned parallel to each other and extending to the bottom side, and e) wherein the at least one complex aperture has a complex aperture distance measured from the center of the first radii to the center of the second radii along the parallel first and second radii and the relief zone disposed between the adjoined first and second screw apertures that is at least equal to a sum of the first and second radii, and f) wherein the two opposed planar surfaces of the relief zone are spaced apart by a lateral distance that is less than twice the distance of the first radii and less than twice the distance of the second radii.

24. The bone plate of claim 23 wherein the respective beveled surfaces of the first and second screw apertures extend downwardly and inwardly from the upper surface to the wall surface at either the same or different angles.

* * * * *